United States Patent [19]

Chabardès et al.

[11] 3,980,695

[45] Sept. 14, 1976

[54] METHYL-PENTENYL SULPHONES

[75] Inventors: Pierre Chabardès, Lyon; Marc Julia, Paris; Albert Menet, La Mulatiere, all of France

[73] Assignee: Rhone-Poulenc S.A., Paris, France

[22] Filed: Apr. 16, 1973

[21] Appl. No.: 351,342

[30] Foreign Application Priority Data

Apr. 18, 1972  France .............................. 72.13588

[52] U.S. Cl. ......................... 260/481 R; 260/456 R; 260/456 P; 260/464; 260/465 D; 260/465 H; 260/465 K; 260/465.4; 260/465.8 R; 260/465.9; 260/468 J; 260/470; 260/514 J; 260/515 M; 260/526 S; 260/534 S; 260/557 R; 260/558 S; 260/561 S; 260/562 S; 260/590 R; 260/590 E; 260/593 R; 260/598; 260/599; 260/601 R; 260/607 A

[51] Int. Cl.² ................ C07C 147/02; C07C 147/04

[58] Field of Search ...................... 260/481 R

[56] References Cited

UNITED STATES PATENTS 3,541,119   11/1970   Richter et al. .................. 260/481 R Primary Examiner—Vivian Garner
Attorney, Agent, or Firm—Stevens, Davis, Miller & Mosher

[57]  ABSTRACT

Sulphones of formula $QSO_2CH_2CY=CY_1CH_2CHRR_1$ wherein one of Y and $Y_1$ is hydrogen the other methyl, R and $R_1$ are CHO, $COR_2$, COOH, $COOR_3$, $CONR_4R_5$, CN, $SO_2R_4$, $SO_3R_5$ and $NO_2$, wherein $R_2$–$R_5$ are alkyl or aryl and $R_5$ can be hydrogen, and Q is alkyl, substituted alkyl, aryl, aralkyl or alkaryl or optionally substituted, optionally unsaturated terpene of 5n carbon atoms (n being 1–9), but excluding 2- or 3-methylbutadienyl and 2-butadienylmethyl, are intermediates for preparing terpenes.

3 Claims, No Drawings

METHYL-PENTENYL SULPHONES

This invention relates to methylpentenyl sulphones.

The present invention provides sulphones of the general formula

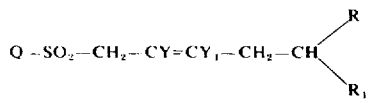 I in which one of the symbols Y and $Y_1$ (preferably $Y_1$) represents a hydrogen atom and the other symbol (preferably Y) represents a methyl radical; each of R and $R_1$, which are the same or different, represents a radical of formula —CHO, —$COR_2$, —COOH, —$COOR_3$, —$CONR_5R_5$, —CN, —$SO_2R_4$, —$SO_3R_5$ and —$NO_2$, wherein each of $R_2$, $R_3$, $R_4$ and $R_5$ represents an alkyl radical (e.g. of 1 to 6 carbon atoms such as methyl and ethyl radicals) or aryl radical (preferably an aromatic hydrocarbon radical of 6–19 carbon atoms such as a phenyl radical) or $R_5$ can also represent a hydrogen atom, and Q represents an alkyl substituted alkyl, aryl, aralkyl or alkylaryl radical or a saturated or unsaturated terpene radical containing $5n$ carbon atoms, $n$ being an integer of 1 to 9, which is substituted or unsubstituted, with the proviso that Q does not represent a 3-methylbutadienyl, 2-methylbutadienyl or 2-butadienylmethyl radical. The terpene radical for Q can be saturated or unsaturated with conjugated and/or unconjugated ethylenic unsaturation and acetylenic unsaturation, and can possess functional groups or be substituted by alkyl groups. When $n$ is 2 or more, Q can contain a ring to which alkyl groups and/or functional groups such as O= or —OH are optionally attached, the functional groups being free or protected.

Q can also contain at least one of the following functional groups: An alcohol group, an ether group derived therefrom (e.g. an alkylether with preferably 1 to 6 carbon atoms in the alkyl group) or an ester group derived therefrom with an inorganic or organic acid, (e.g. an alkanoic acid with preferably 1 to 6 carbon atoms) or a halogen, e.g. chlorine or bromine, a free or protected aldehyde group, an acid group (e.g. $CO_2H$) or a derivative thereof, such as an acid chloride (e.g. COCl), ester (e.g. $COOR_7$ wherein $R_7$ is an organic radical), amide (e.g. $CONR_8R_9$ wherein $R_8$ and $R_9$ are organic radicals or hydrogen) or nitrile e.g. CN, a —SR' or $SO_2R'$ group in which R' represents an alkyl, alkaryl, aryl or aralkyl radical, preferably as defined below for Q when an alkyl, aryl, alkenyl or aralkyl radical.

The group Q is usually a saturated or unsaturated aliphatic radical or aryl radical. Q preferably contains up to 15 carbon atoms, when it represents an alkyl or substituted alkyl radical and 6–19 carbon atoms when it represents the aryl, aralkyl or alkaryl radical, which is preferably a hydrocarbon radical, e.g. a phenyl, alkylphenyl or phenylalkyl radical with preferably 1 to 4 carbon atoms in the alkyl group.

The terpene radical represented by Q preferably represents a group having a carbon skeleton of formula;

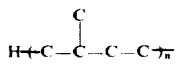

wherein $n$ is 1–9, each $C_5$ unit containing 0–2 ethylenic double bonds and 0–1 acetylenic bonds, the remaining valencies being satisfied by hydrogen atoms, or two adjacent $C_5$ units are joined to form a structure containing a ring of 6 ring carbon atoms, which can be substituted by a hydroxy or oxo group, or by a methyl group additional to the methyl substituents forming part of the carbon skeleton of $C_5$ units. The ring is usually a 2,6,6-trimethylcyclohex-1-enyl ring. Examples of the terpene radicals are 3-methyl-but-2-enyl, geranyl and retinyl radicals.

The compounds of the formula I can be prepared by various methods, starting especially from compounds of the formula R—$CH_2$—$R_1$ with compounds containing a sulphone group of formula Q—$SO_2CH_2$—CY=λ $CY_1$—$CH_2X$ or $QSO_2CH$=CY—$CY_1$=$CH_2$, as further described below, in the presence of a basic agent.

One of these methods consists of reacting the compound R—$CH_2$—$R_1$ with a halogenosulphone corresponding to the formula Q—$SO_2$—$CH_2$—CY=λ CY—$CH_2X$, in the presence of a basic agent, which can be inorganic or organic. The reaction can be represented by the equation:

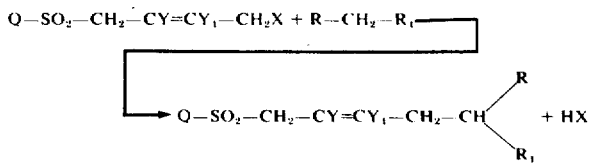

The halogenosulphones used are in particular chlorosulphones and bromosulphones, such as 1-chloro-2-methyl-4-phenylsulphonyl-2-butene or 1-chloro-3-methyl-4-phenylsulphonyl-2-butene.

Compounds of formula $QSO_2$—$CH_2$—CH=C(CH-$_3$)—$CH_2X$ which can be used in this process, wherein Q represents an alkyl, alkenyl, aralkyl, alkaryl or aryl radical, each of which radicals may be substituted by at least one electron donor or acceptor substituent are described and claimed in application Ser. No. 328,600 filed 1st Feb. 1973 in which Q represents a hydrocarbon radical or preferably an optionally substituted alkyl or aryl radical. These compounds may be prepared by reacting a 1,4-dihalo-3-methyl-but-2-ene with an alkali metal sulphinate of formula $QSO_2M$.

The compounds R—$CH_2$—$R_1$, which contain an activated methylene group, can be malonic acid derivatives such as malonic aldehyde, malonic acid, its esters or its salts, malononitrile, acetylacetone, acetylacetic acid, its esters or its salts, alkyl cyanoacetates and sulphonylacetones.

Amongst the suitable basic agents are alkali metal hydroxides and carbonates, alkali metal alcoholates (e.g. with alkanols of 1 to 6 carbon atoms) and organic bases such as amines, e.g. those listed below, and quaternary ammonium hydroxides. The alkali metal is usually sodium or potassium. The reaction is preferably carried out in a solvent such as an aliphatic alcohol, an ether or an aliphatic or aromatic hydrocarbon. An advantageous method of carrying out the reaction consists of using an alcoholic solution of an alkali metal alcoholate as the basic agent.

Another of the methods for making the sulphones of formula I comprises reacting the methylene compound of formula R—CH$_2$—R$_1$ with a diene sulphone of the formula Q—SO$_2$—CH=CY—CY$_1$=CH$_2$, in the presence of a basic catalyst, according to the equation:

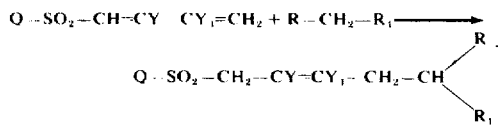

Amongst the suitable diene sulphones are alkyl (or aryl) 4-sulphonyl-2-methyl-butadienes, alkyl (or aryl) 4-sulphonyl-3-methyl-butadienes, 4-isoprenylsulphonylmethyl-butadienes, 4-geranylsulphonyl-methyl-butadienes and 4-retinylsulphonylmethyl-butadienes. These diene sulphones can be prepared by reacting an alkyl halide Q-X with an alkali metal isoprenylsulphinate, in accordance with one of the usual methods for the preparation of sulphones.

Diene compounds of formula QSO$_2$CH=$_3$)—CH=CH$_2$, which may be used in this process for preparing the sulphones of the invention, wherein O represents an optionally substituted terpene group of 5n carbon atoms (n being an integer of 1–9) are described and claimed in our application Ser. No. 351,343 filed Apr. 16th 1973, now U.S. Pat. No. 3,890,393. These compounds may be prepared by reacting a halide of formula QX with an alkali metal isoprenyl sulphinate, or a hydroxy compound of formula QOH with isoprenylsulphinic acid.

Diene compounds of formula QSO$_2$CH=λ CH—C(CH$_3$)=CH$_2$ which can be used in the diene process for making the sulphones of the invention wherein Q represents an alkyl, alkenyl, aralkyl, alkaryl or aryl radical, each of which radical may be substituted by at least one electron donor or acceptor substituent, are described and claimed in Pat. appln. Ser. No. 349,172 filed Apr. 9th, 1973, now U.S. Pat. No. 3,876,707. They may be prepared by reacting 4-chloro(or bromo)-3-methyl but-2-enyl sulphones (i.e. of formula QSO$_2$CH$_2$—CH=C(CH$_3$)—CH$_2$X wherein X represents chlorine or bromine) with a base.

The reaction between the diene sulphone and the methylene compound is carried out in the presence of inorganic or organic alkaline agent, such as an alkali metal hydroxide or alcoholate (e.g. with an alkanol of 1 to 6 carbon atoms), an amine such as a secondary or tertiary amine, e.g. diethylamine, diisopropylamine, pyridine, triethylamine and tributylamine, or a quaternary ammonium hydroxide e.g. benzyltrimethyl ammonium hydroxide. The alkali metal is usually sodium or potassium. The reaction can be carried out with or without a solvent. It is however preferable to choose a solvent so that the reaction takes place in a homogeneous phase. This solvent can be an alcohol e.g. of 1 to 6 carbon atoms such as methanol, ethanol or tertiary butyl alcohol, or an ether such as diethyl ether, dioxan or tetrahydrofuran, or any other inert solvent such as benzene, toluene, dimethylformamide, or acetonitrile.

The reaction takes place at ambient temperature; when the reaction products are not affected by heating, the reaction can be accelerated by working at a higher temperature. If the reaction products are sensitive to heat, the reaction can be carried out at temperatures below ambient temperature. A description of all the working conditions relating to the Michael reaction, of which the present process is an application, will be found in "Organic Reactions, volume 10. p. 264–266 - The Michael Reaction".

In addition to their sulphone functions, the sulphones of the invention contain one or two of the groups listed for R and R$_1$, and therefore are of value in the synthesis of polyisoprene compounds of various degrees of saturation, belonging, for example. to the family of geraniol, ionones and pseudoionones, retinene, apocarotenes and the like.

The new sulphones may be polymerised by heating in a solvent in the presence of peroxidic compounds. The polymers obtained are particularly useful for enzyme insolubilization : owing to their functionnal groups, the polymers may be caused to react with enzymes. The reaction is effected by application of conventional methods, depending upon the nature of enzyme and functional group of the polymer. Polymers may be also obtained according to J. Polym. Sci., Polym. Let. Ed., 10 p. 929–933 (1972).

When the symbol Q in formula I is an aliphatic radical, the new sulphones may be desulphonated according to the Meyer reaction (treatment by a mixture comprising water, t.butanol, carbon tetrachloride and caustic potash). The desulphonation reaction leads to compounds as dehydropseudoionone, dehydrophytone, which like pseudoionone and phytone may be used to produce vitamin E according to conventional methods.

The new sulphones of formula I in which Q is an aliphatic radical R is CN and R$_1$ is COOR$_3$ may be desulphonated as described herein above. Then, products with fragrance like lemon may be obtained after saponification and decarboxylation by heat treatment in alkaline medium of desulphonated products.

The new sulphones of formula I in which Q is aryl or alkylaryl, Y is methyl and Y$_1$ is hydrogen may be reacted with α,β-unsaturated β-methylated aliphatic primary halides. The reaction is effected in an organic solvent in the presence of an alkaline alcoholate and gives products utility of which is the same as the utility of products described in our application Ser. No. 328,537 filed Feb. 1st 1973.

The new sulphones of formula I in which Q is aryl or alkylaryl, Y is hydrogen and Y$_1$ is methyl, may be reacted with α,β-unsaturated β-methylated aliphatic primary halides in the fore-mentioned way to give products utility of which is the same as the utility of products described in our application Ser. No. 328,624 filed Feb. 1st 1973, now U.S. Pat. No. 3,850,991.

The following Examples illustrate the invention.

EXAMPLE 1

2.08 g. of 1-phenylsulphonyl-2-methyl-butadiene, 1.5 g. of redistilled ethyl acetylacetate (boiling point $_{1.5}$ = 70°C.), 0.4 cm$^3$ of a 40% by weight solution of trimethylbenzyl-ammonium hydroxide (TRITON B) in methanol and 40 cm$^3$ of acetonitrile are introduced into a flask kept at 25°C. The mixture is stirred overnight, under an atmosphere of nitrogen. The mixture is then diluted with 200 cm$^3$ of water, neutralised with acetic acid and then extracted 3 times with diethyl ether and washed 3 times with a saturated solution of sodium chloride. The reaction mixture is then dried over magnesium sulphate and the solvent is driven off in vacuo. 3.56 g. of a crude residue are thus obtained, from which 132 mg. of a product corresponding to the formula:

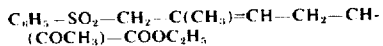

are isolated by thin layer chromatography (support: silica; elutant: methylene chloride/cyclohexane in a 50/50 volume ratio).
Yield: 27%.

1-Phenylsulphonyl-2-methyl-butadiene was prepared according to the process described in the Journal of Organic Chemistry, 35, pg. 4219 (1970).

EXAMPLE 2

0.2 g. of a 40% by weight solution of trimethylbenzylammonium hydroxide (TRITON B) in methanol is added to a solution of 1.13 g. of ethyl cyanoacetate in 10 cm$^3$ of acetonitrile. The mixture is cooled to 10°C and a solution of 2.08 g. of 1-phenylsulphonyl-2-methyl-butadiene in 7 cm$^3$ of acetonitrile is run in over the course of 10 minutes.

The temperature is allowed to rise to 23°C. again and the reaction mixture is stirred for several hours and then poured onto a mixture of 70 cm$^3$ of water and 30 cm$^3$ of diethyl ether. The combined ether layers are washed with water, dried over magnesium sulphate, filtered and concentrated. A colourless viscous product is thus obtained, which contains 2.6 g. of a sulphone corresponding to the formula:

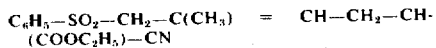

Degree of conversion: 100%. Yield relative to the starting sulphone: 81%.

EXAMPLE 3

0.650 g (5 × 10$^{-3}$ mol) of ethyl acetylacetate and 10 cm$^3$ of acetonitrile are introduced into a 50 cm$^3$ three-necked flask equipped with a stirrer, a condenser, a dropping funnel and a nitrogen flow system. 0.250 g. of a 40% by weight solution of trimethylbenzylammonium hydroxide (TRITON B) in methanol, dissolved in 3 cm$^3$ of acetonitrile, is added at +20°C.

The mixture is cooled to +10°C and a solution of 1 g (5 × 10$^{-3}$ mol) of the sulphone of the formula:

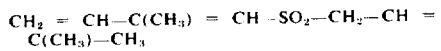

in 5 cm$^3$ of acetonitrile is run in over the course of 10 minutes. The mixture is kept at +10°C for 50 minutes and at 23°C for 3 hours.

The reaction mixture is poured into a mixture of 25 cm$^3$ of water and 25 cm$^3$ of diethyl ether. The mixture is decanted and extracted with twice 20 cm$^3$ of diethyl ether. The ether layers are washed with 3 times 20 cm$^3$ of water, dried over magnesium sulphate, filtered and concentrated.

A whitish liquid is obtained, which contains 0.460 g. of unconverted sulphone and 0.800 g. of product, corresponding to the formula

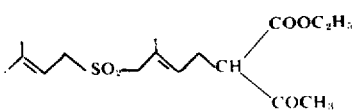

Degree of conversion of the starting sulphone: 54%.
Yield relative to the sulphone converted: 90%.

The starting sulphone was prepared by adding 2.98 g. of 1-bromo-3-methyl-2-butene to 2.64 g. of 1,1-dioxy-2,5-dihydro-3-methyl-thiophene (also known as cyclic isoprenesulphone), in the presence of 2.24 g. of potassium t-butylate in 20 cm$^3$ of tetrahydrofuran, followed by heating at 70°C for 4 hours.

EXAMPLE 4

Following the procedure of the preceding Example, 0.80 g. of diethyl malonate, is reacted with 1 g. of the same sulphone, in 10 cm$^3$ of acetonitrile, and the same amount of TRITON B dissolved in methanol. The reaction mixture is then treated in the same way and 1.04 g. of a whitish liquid product, corresponding to the formula:

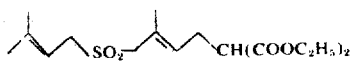

are thus isolated.

Degree of conversion of the starting sulphone: 100%.
Yield: 57%.

EXAMPLE 5

26 g. of ethyl acetylacetate are added to 200 cm$^3$ of ethanol treated with 4.6 g. of sodium metal. The mixture is stirred for 30 minutes and then 24.5 g. of phenyl-4-chloro-2-methyl-2-butenyl-sulphone, dissolved in 200 cm$^3$ of ethanol, are added. The mixture is stirred for 1 hour at 25°C and then heated under reflux for 2 hours. The ethanol is evaporated in vacuo, and the residue is taken up in water and then extracted with diethyl ether. The product is washed with a saturated solution of sodium chloride until neutral, dried over magnesium sulphate and then evaporated. 32.6 g. of a solid product are obtained, in which 84% of the same compound as that obtained in Example 1 is measured by thin layer chromatography.

Phenyl-4-chloro-2-methyl-2-butenylsulphone was prepared according to the process described in the Journal of Organic Chemistry 35, 4218 (1970).

EXAMPLE 6

A mixture of 1.32 g. of dimethyl malonate, 10 cm$^3$ of methanol and 0.23 g. of sodium is heated at 60° for one hour, with stirring. After cooling, 2.44 g. of phenyl-4-chloro-2-methyl-2-butenyl-sulphone, diluted with 10 cm$^3$ of methanol, are added and the mixture is stirred at ambient temperature for several hours. The methanol is removed and the residue is taken up in water and extracted with 3 times 50 cm$^3$ of diethyl ether. The combined ether layers are treated as in the preceding Examples and a crystalline product, of melting point 58°C, identified by IR spectrography and NMR as being of the formula:

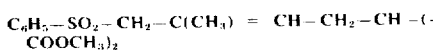

is isolated therefrom.

EXAMPLE 7

0.8 g. of dimethyl malonate and 1 g. of phenyl-1-sulphonyl-2-methyl-butadiene, in 10 cm³ of acetonitrile and in the presence of 0.1 g. of TRITON B, are reacted under conditions identical to those of Example 1. The reaction mixture is then poured onto iced water and extracted with 3 times 50 cm³ of diethyl ether. On treating the combined ether layers, a product of melting point 58°C, which has the formula:

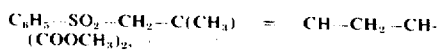

is isolated.

EXAMPLE 8

5 g. of acetylacetone are run into a solution of sodium ethanolate which has been prepared from 50 cm³ of absolute ethanol and 1.15 g. of sodium metal. The mixture is cooled and stirred for 30 minutes at ambient temperature. A solution of 12.2 g. of phenyl-4-chloro-2-methyl-2-butenyl-sulphone in 50 cm³ of absolute ethanol is then run in and the whole is heated under reflux (78°C) for 3 hours. The alcohol is removed in vacuo and the residue is taken up in 100 cm³ of water and then extracted with diethyl ether and the ether layers are treated as in the previous Examples. 10.8 g. of a viscous product are obtained, in which 40% of a product of the formula

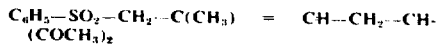

is identified and measured by NMR.

EXAMPLE 9

A solution of 0.65 g. of ethyl acetylacetate in 5 cm³ of tetrahydrofuran is added, over the course of 2 minutes, to 0.915 g. of potassium t-butylate in 5 cm³ of tetrahydrofuran. A solution of 1.34 g. of 1-(2-methyl-butadienyl-sulphonyl)-3,7-dimethyl-2,6-octadiene in 10 cm³ of tetrahydrofuran is then run in over the course of 3 minutes and the whole is stirred for 1 hour 40 minutes at 25°C.

The reaction mixture is poured into a mixture of 25 cm³ of water and 25 cm³ of diethyl ether. The mixture is decanted and the aqueous layer is extracted with twice 20 cm³ of diethyl ether. The combined ether layers are treated as above and a red oil containing 1.6 g. of a product of the formula:

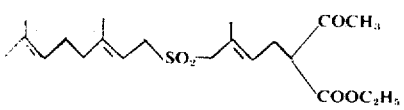

is isolated therefrom.

Degree of conversion: 100%.
Yield: 80%.

The starting sulphone was prepared by keeping a solution of 44 g. of geranyl bromide in 30 cm³ of methanol and a solution of 34.7 g of potassium 2-methyl-butadienylsulphinate in 100 cm³ of dimethylsulphoxide in contact at ambient temperature and with stirring.

Potassium 2-methyl-butadienyl-sulphinate was prepared by reacting potassium t-butylate with cyclic isoprene sulphone.

We claim:
1. A sulphone of the formula:

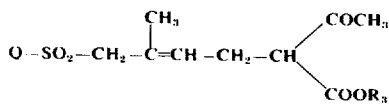

in which $R_3$ is ethyl and
Q is 3-methylbut-2-enyl or geranyl.
2. 7-(3-Methyl-2-butenyl-sulphonyl)-6-methyl-3-ethoxycarbonyl-hept-5-en-2-one.
3. 7-Geranylsulphonyl-6-methyl-3-ethoxycarbonyl-hept-5-en-2-one.

* * * * *